(12) United States Patent
Hussein

(10) Patent No.: US 12,195,645 B2
(45) Date of Patent: Jan. 14, 2025

(54) HOT-MELT ADHESIVE FOR MANUFACTURING DISPOSABLE HYGIENE PRODUCTS

(71) Applicant: BOSTIK SA, Colombes (FR)

(72) Inventor: Naji Hussein, Venette (FR)

(73) Assignee: BOSTIK SA, Colombes (FR)

( * ) Notice: Subject to any disclaimer, the term of this patent is extended or adjusted under 35 U.S.C. 154(b) by 715 days.

(21) Appl. No.: 17/294,241

(22) PCT Filed: Nov. 5, 2019

(86) PCT No.: PCT/EP2019/080238
§ 371 (c)(1),
(2) Date: May 14, 2021

(87) PCT Pub. No.: WO2020/099187
PCT Pub. Date: May 22, 2020

(65) Prior Publication Data
US 2022/0017796 A1   Jan. 20, 2022

(30) Foreign Application Priority Data
Nov. 15, 2018 (EP) ..................... 18306496

(51) Int. Cl.
| C09J 153/02 | (2006.01) |
| A61L 15/58 | (2006.01) |
| C09J 5/06 | (2006.01) |
| C09J 11/06 | (2006.01) |

(52) U.S. Cl.
CPC .......... *C09J 153/02* (2013.01); *A61L 15/585* (2013.01); *C09J 5/06* (2013.01); *C09J 11/06* (2013.01); *C09J 2203/358* (2020.08); *C09J 2301/304* (2020.08); *C09J 2301/408* (2020.08); *C09J 2423/00* (2013.01); *C09J 2453/00* (2013.01)

(58) Field of Classification Search
CPC ... C09J 153/02; C09J 5/06; C09J 11/06; C09J 2203/358; C09J 2301/408; C09J 2301/304; C09J 2423/00; A61L 15/585
See application file for complete search history.

(56) References Cited

U.S. PATENT DOCUMENTS

| 4,680,333 A | 7/1987 | Davis |
| 5,714,254 A | 2/1998 | Lutz |
| 9,242,437 B2 | 1/2016 | Goubard et al. |
| 11,375,771 B2 | 7/2022 | Lehmann et al. |
| 2011/0281045 A1 | 11/2011 | Goubard et al. |
| 2013/0184384 A1 | 7/2013 | Liu et al. |
| 2017/0166785 A1* | 6/2017 | Hussein ............... C09J 11/06 |

FOREIGN PATENT DOCUMENTS

| JP | 2013082827 | * 10/2011 | ............ C09J 201/00 |
| WO | 2008063623 A2 | 5/2008 | |
| WO | WO-2012068573 A2 * | 5/2012 | ............. C08L 23/06 |
| WO | 2018140307 A2 | 8/2018 | |

OTHER PUBLICATIONS

International Search Report for PCT/EP2019/080238 dated Jan. 21, 2020.

* cited by examiner

*Primary Examiner* — Shane Fang
(74) *Attorney, Agent, or Firm* — Millen White Zelano & Branigan; Csaba Henter

(57) ABSTRACT

1) Hot melt adhesive composition comprising:
 a) from 5% to 50% of a thermoplastic polymer (A) selected from styrene block copolymers and polyolefins;
 b) from 15% to 60% of a tackifying resin (B);
 c) from 5% to 30% of a plasticizer (C); and
 d) from 0.1% to 10% of a salt (D) of a hydroxylated fatty acid comprising from 8 to 24 carbon atoms.

2) Process of manufacturing a laminate, preferably a disposable nonwoven absorbent article, implementing the hot melt adhesive composition.

3) Process for cleaning the laminating device fouled by solid deposits of the hot melt adhesive composition, comprising their manual removal by the operators at room temperature.

20 Claims, No Drawings

HOT-MELT ADHESIVE FOR MANUFACTURING DISPOSABLE HYGIENE PRODUCTS

The subject matter of the present invention is a hot-melt adhesive composition which is suitable for a process of manufacturing of disposable hygiene products and which advantageously provides an easy cleaning of the metallic parts of the manufacturing equipment which have been fouled by the hot-melt adhesive composition during said process.

Hot-melt adhesives (HM adhesives) are substances which are solid at ambient temperature and which comprise neither water nor solvent. They are applied in the molten state after heating to a temperature generally of between 100 and 250° C., most often between 130 and 180° C., and solidify during cooling, thus forming a seal (or adhesive joint) which ensures the attachment of the two substrates to be assembled. Hot-melt adhesives are generally provided in the form of compositions which comprise a thermoplastic polymer and optionally a tackifying resin and a plasticizer.

Some HM are formulated in such a way as to give to the corresponding coated substrate a relatively hard and tackless character. Other HM result in coated substrates with a relatively soft character and a high tack: these HM are Pressure Sensitive Adhesives (or PSA) which are largely used for the manufacturing of PSA labels. Such adhesives are designated under the name of Hot Melt Pressure Sensitive Adhesive (or HMPSA).

U.S. Pat. No. 4,680,333 describes a removable HMPSA prepared from styrene-isoprene-styrene block copolymers, low softening point aliphatic resins and metallic salts of fatty acids such as zinc or calcium stearates. This HMPSA is useful for labelling and provides excellent tack and adhesion, yet with no adhesion build up on aging so that the bonded substrates may be readily and clearly separated when desired. Said HMPSA does not provide for permanent assembly of substrates.

Hot-melt adhesive compositions other than removable HMPSA are used industrially in a wide range of applications, such as, for example, the manufacture of rigid packagings based on paper and board, the creation of bindings in the publishing industry, the production of various assemblies in the fields of electronics, motor vehicles or textiles, or the manufacture of disposable hygiene articles.

The latter field relates in particular to disposable diapers and to feminine protection products. Hot-melt adhesives are used therein for the preparation of permanent assemblies of thin sheets and of porous substrates of different materials by laminating. Mention may be made, as example of such permanent assemblies, in the case of diapers, of the lamination of a PolyEthylene (PE) sheet with a nonwoven cloth of PolyPropylene (PP), the latter giving a silky appearance pleasing to the eye and to the touch.

The required level of cohesion for such permanent assemblies (or laminates) is usually quantified by a "peel" and/or a "shear" test.

The laminating of such sheets (or substrates) is carried out industrially by a process which comprises:
  the heating (to a temperature of between 100 and 250° C. and preferably between 130 and 180° C.) of the hot-melt adhesive composition in a vat (referred to as melting pot or tank), until it becomes molten, then
  the coating of one of the two substrates to be assembled, resulting in the deposition, by means of a nozzle, of a layer of said composition in the molten state, the thickness of which is controlled and is generally between 1 and 500 µm, and finally
  bringing the substrate thus coated into contact, under pressure such as provided for example by nip rolls, with the substrate to be laminated or assembled.

The equipment used for the implementation of such a laminating process is generally a machine (or coater) which operates continuously with often high line speeds and in which, for example, both the components to be laminated or assembled (sheets, films or other substrates) and the final product, often denoted by the term of "complex" or "laminate", are, due to their very large dimensions, packaged by winding off in the form of reels of large width and diameter.

The stage of coating with the molten hot-melt adhesive composition comprises passing it through one or more nozzles at a high pressure, of the order of a few bar to more than 100 bar, so as to obtain good contact (or wetting) with the substrate to be coated, which wetting contributes to giving the necessary level of cohesion to the final permanent assembly of the two substrates.

Depending on the inherent hot-melt adhesive properties (such as viscosity or rheology) and the coater machine parameters (such as temperature or nozzle air pressure), the hot-melt adhesive can be sprayed, in the case of a spray nozzle, outside the desired coated area resulting in an undesirable contact, through adhesive scattering, between the hot melted adhesive composition and some metallic parts of the equipment, which contact results in the fouling/contamination of these metallic parts, by the sticky deposits which are formed after the cooling down and solidification of the melted adhesive.

Another issue resulting in such fouling frequently comes from the undesirable drooling phenomenon occasionally observed when slot dies (or slot nozzles) are used in the coater machine. This drooling phenomenon results from the uncontrolled leakage of the adhesive outside the slot nozzle.

Another reason yet for such fouling is frequently reported by the manufacturers of disposable hygiene articles. It is linked to the bleed through phenomenon, corresponding to the bleed through of the adhesive between the two laminated substrates or through the porous substrates, at the nip rolls level.

As a consequence of such fouling, operators must frequently interrupt the production lines for maintenance and cleaning, particularly in order to remove the sticky deposits of the solid adhesive composition which adhere to the metallic surfaces of the coating machine. These frequent interruptions and cleaning operations result in a lower productivity for the disposable hygiene products (like diapers) manufacturing.

Therefore, one aim of the present invention is to provide a hot-melt adhesive composition which avoids these drawbacks.

Another aim of the present invention is to provide a hot-melt adhesive composition suitable for a laminating process, which, after fouling some metallic surfaces of the laminating equipment, can be easily cleaned/removed/wiped out at room temperature by the manufacturing operators.

Another aim of the present invention is to provide a hot-melt adhesive composition which makes it possible to obtain, for the assembling (or laminating) of two substrates, an acceptable and/or improved level of cohesion at the temperature of use of the complex product, which generally lies in a temperature range close to ambient.

Another aim of the present invention is to provide a hot-melt adhesive composition which makes it possible to maintain such a level of cohesion after storage of the complex product over time in various temperature conditions.

In addition, it is also necessary for the hot-melt adhesive composition employed in the laminating process to exhibit certain physicochemical characteristics which render it suitable for this use.

Thus said composition, which is prepared by the hot mixing of its various ingredients, must remain homogeneous (or stable) at the temperature corresponding to the various stages of the laminating process, in particular from the melting pot to the coating nozzles. This thermal stability must also be maintained over time as the manufacturers of disposable hygiene articles may be driven to store the composition in the molten state in the melting pot for up to three days.

Therefore, another aim of the present invention is to provide a hot-melt adhesive composition which is stable up to the high temperature of the melting tank, for example up to a temperature of greater than 130° C., preferably equal to approximately 180° C., and the homogeneous nature of which is maintained after storage at this temperature for a few days, for example up to 3 days. Such homogeneity is preferably assessed by a stable viscosity, measured at 149° C.

It has now been found that the above aims can be achieved in all or in part by means of the hot-melt adhesive composition which is the subject matter of the present invention.

According to a first object of the invention, the present application relates to a hot melt adhesive composition comprising:
  a) from 5% to 50% by weight of at least one thermoplastic polymer (A) selected from styrene block copolymers (SBC) and polyolefins;
  b) from 15% to 60% by weight of at least one tackifying resin (B);
  c) from 5% to 30% by weight of at least one plasticizer (C) selected from a naphthenic oil, a paraffinic oils, polyisobutylene, a benzoate ester, a wax and an acrylic or carboxylic acid modified wax; and
  d) from 0.1% to 10% by weight of a salt (D) of a hydroxylated fatty acid comprising from 8 to 24 carbon atoms.

More preferably, the present application relates to a hot melt adhesive composition characterized in that it consists essentially:
  a) from 5% to 50% by weight of the thermoplastic polymer (A);
  b) from 15% to 60% by weight of the tackifying resin (B);
  c) from 5% to 30% by weight of the plasticizer (C); and
  d) from 0.1% to 10% by weight of the salt (D) of the hydroxylated fatty acid; the total content of the above mentioned ingredients totaling 100% by weight.

The contents of the above mentioned ingredients (A to D) in the hot melt adhesive composition, given in percentage by weight, are expressed relatively to the total weight of the hot melt adhesive composition.

It has been surprisingly found that, due to its strongly reduced adhesion to metal, the hot melt adhesive composition subject of the invention which, during the lamination process and at the molten state, has come to foul/contaminate metallic parts of the lamination equipment can be, after cooling down to the solid state, easily wiped out by the manufacturing operators. This results in shorter maintenance operations.

At the same time, said hot melt adhesive provides laminates with high level cohesion, in particular thanks to its strong adhesion to non metallic substrates, and more particularly to polymeric substrates. Finally, said hot melt is homogenous and physically and thermally stable, in particular viscosity stable, in the coater melting tank, during the industrial implementation of the laminating process, and in particular during up to three days, which is quite advantageous in terms of conduct, flexibility and productivity of said process.

Thermoplastic Polymer (A):

The hot melt adhesive composition according to the invention comprises from 5% to 50% by weight of at least one thermoplastic polymer (A) which is selected among styrene block copolymers (SBC) and polyolefins.

In a first embodiment, the thermoplastic polymer(s) (A) is a SBC.

Styrene block copolymer(s) useful according to the invention include linear or radial block copolymers comprising at least one non elastomeric block A being a polystyrene block and at least one elastomeric block B being a totally or partially hydrogenated or a non hydrogenated diene polymer block.

In particular, styrene block copolymer according to the invention may be chosen from the following copolymers, and mixtures thereof:
  linear diblock copolymer of AB structure,
  linear triblock copolymer of ABA structure,
  radial block copolymers of the $(AB)_n Y$ structure, wherein:
  A is a non elastomeric polystyrene block,
  B is an elastomeric diene block polymer such as polybutadiene or polyisoprene block,
  Y is a multivalent compound, and
  n is an integer of at least 3.

The linear triblock copolymer of ABA structure may be used alone or in mixture with a linear diblock copolymer of AB structure.

The elastomeric block B can be post treated through partial or total hydrogenation to improve its heat stability.

Preferably, the styrene block copolymer useful according the invention is chosen from the following linear triblock copolymers:
  styrene-butadiene-styrene copolymer (SBS) with or without styrene-butadiene diblock (SB),
  styrene-isoprene-styrene copolymer (SIS) with or without styrene-isoprene diblock (SI),
  styrene-ethylene-butylene-styrene copolymer (SEBS),
  styrene-butadiene-butylene-styrene copolymer (SBBS),
  styrene-ethylene-propylene-styrene copolymer (SEPS),
  and any mixture thereof.

More preferably, the styrene block copolymer is a linear triblock copolymer of ABA structure, as defined above, and even more preferably a linear SIS or SBS triblock copolymer. When the styrene block copolymer is a mixture of linear triblock copolymer of ABA structure and linear diblock copolymer of AB structure, as defined above, the linear diblock content preferably ranges from 1 to 70% by weight relative to the total weight of the triblock and diblock mixture.

The amount of the end blocks A in the linear triblock copolymer of ABA structure, as defined above, may range from 14 to 51% by weight, preferably from 20 to 40% by weight, relative to the total weight of the linear triblock copolymer of ABA structure or, in the case of a mixture of linear triblock and diblock copolymers of ABA and AB structures, relative to the total weight of the triblock and diblock mixture.

Useful commercial styrene block copolymers include KRATON D and G® series from KRATON POLYMERS, EUROPRENE Sol T® series from VERSALIS (ENI group), SOLPRENE® series from DYNASOL ELASTOMERS, and TAIPOL® and VECTOR® seriesfrom TSRC Corporation.

As example of useful specific styrene block copolymers, mention may be made of:
- KRATON® D1152ES, a mixture of linear SBS triblock and SB diblock copolymers, with a styrene content of 29.5% by weight relative to the total weight of the mixture, an average molecular weight of around 122 000 g/mol, a MFI (measured according to ISO1133) of 8.5 grams (g)/10 minutes (mn) at 200° C. under a load of 5 kilograms (kg), and a SB diblock content of around 17% by weight relative to the total weight of the mixture.
- KRATON® D1161, a mixture of linear SIS triblock and SI diblock copolymers, with a styrene content of 15% by weight relative to the total weight of the mixture, a MFI (measured according to ISO1133) of 9 g/10 mn at 200° C. under a load of 5 kg, an average molecular weight of around 220 000 g/mol, and a SI diblock content of around 19% by weight relative to the total weight of the mixture.
- TAIPOL® SBS 4202 from TSRC Corporation, a linear SBS triblock copolymer with a styrene content of 40% by weight relative to the total weight of the triblock copolymer, a SBdiblock content of less than 1%, a MFI (measured according to ASTM D1238) of 3-10 g/10 nm at 190° C. under a load of 5 kg, an average molecular weight of around 102 400 g/mol.
- VECTOR® 4411 from TSRC Corporation, a linear SIS triblock copolymer with a styrene content of 44% by weight relative to the total weight of the triblock copolymer, a SI diblock content of less than 1%, a MFI (measured according to ASTM D1238) of 40 g/10 mn at 200° C. under a load of 5 kg, an average molecular weight of around 106 000 g/mol.

In a second embodiment, the thermoplastic polymer(s) (A) is a polyolefin.

The polyolefin(s) which may be used according to the present invention include:
- copolymer(s) of ethylene and alphaolefin monomers, copolymer(s) of ethylene and non-alphaolefin monomers, and any mixture thereof,
- homopolymer and copolymer of but-1-ene, and any mixture thereof,
- copolymer(s) of ethylene and vinyl acetate (EVA), copolymer(s) of ethylene and acrylate, copolymer(s) of ethylene and methacrylate, copolymer(s) of ethylene and methyl acrylate, copolymer(s) of several of these monomers, and any mixture thereof.

The polyolefin(s) which may be used according to the invention are commercially available under a variety of trade designations including AFFINITY®, VERSIFY® and INFUSE® series from DOW CHEMICAL, VESTOPLAST® series from EVONIK INDUSTRIES AG, VISTAMAXX® series from EXXONMOBIL CHEMICAL, LICOCENE® from CLARIANT and L-MODU® from IDEMITSU KOSAN, EVATANE® series and LOTRYL® series from ARKEMA.

According to a more preferred embodiment, the thermoplastic polymer(s) A is one or more copolymers of ethylene and α-olefin monomers, and even more preferably a copolymer of ethylene and 1-octene.

As example of useful specific copolymers of ethylene and 1-octene, mention may be made of:
- INFUSE® 9807 which is a block copolymer of ethylene and 1-octene, and
- AFFINITY® GA 1900 which is a random copolymer of ethylene and 1-octene.

The total amount of thermoplastic polymer(s) (A) used according to the invention preferably ranges from 15% to 45% by weight, and even more preferably from 15% to 25% by weight, relative to the total weight of the hot melt adhesive composition.

Tackifying Resin (B):

The hot melt adhesive composition according to the invention comprises from 15% to 60% by weight of at least one tackifying resin (B).

Said tackifying resin(s) (B) may comprise one or several carbon-carbon double bond(s) or may comprise no carbon-carbon double bond. In this latter case, saturated tackifying resin(s) may be prepared by total hydrogenation of the insaturated tackifying resin(s).

The tackifying resin (B) is preferably selected among:
(a) natural and modified rosins such as, for example, gum rosins, wood rosins, tall-oil rosins, distilled rosins, hydrogenated rosins, dimerized rosins and polymerized rosins;
(b) glycerol and pentaerythritol esters of natural and modified rosins, such as, for example, the glycerol esters of pale wood rosin, the glycerol esters of hydrogenated rosin, the glycerol esters of polymerized rosin, the pentaerythritol esters of pale wood rosin, the pentaerythritol esters of hydrogenated rosin, the pentaerythritol esters of tall oil rosin and the phenolic modified pentaerythritol esters of rosin;
(c) polyterpene resins include hydrogenated polyterpene resins having a Ring and Ball softening point of from about 20° C. to 140° C., the latter polyterpene resins generally resulting from the polymerization of terpene hydrocarbons, such as the monoterpene known as pinene, in the presence of Friedel-Crafts catalysts at moderately low temperatures;
(d) phenolic-modified terpene resins such as, for example, those resulting from the condensation, in an acidic medium, of a terpene and a phenol;
(e) aliphatic (including cycloaliphatic) petroleum hydrocarbon resins (C5) having a Ring and Ball softening point of from about 60° C. to 140° C., said resins resulting from the polymerization of C5-hydrocarbon monomers; and the corresponding hydrogenated derivatives resulting from a subsequent total or partial hydrogenation thereof;
(f) aromatic petroleum hydrocarbons resins (C9) having Ring and Ball softening point of from about 60° C. to 140° C., said resins resulting from the polymerization of C9-hydrocarbon monomers; and the corresponding hydrogenated derivatives resulting from a subsequent total or partial hydrogenation thereof;
(g) aliphatic (including cycloaliphatic) and/or aromatic petroleum resins (C5/C9) having a Ring and Ball softening point of from about 60° C. to 140° C., said resins resulting from the polymerization of C5/C9-hydrocarbon monomers; and the corresponding hydrogenated derivatives resulting from a subsequent total or partial hydrogenation thereof.

As example of C5-hydrocarbon monomers useful to prepare the tackifying resins belonging to class (e) or (g), mention may be made of trans-1,3-pentadiene, cis-1,3-pentadiene, 2-methyl-2-butene, dicyclopentadiene, cyclopentadiene, cyclopentene, and any mixture thereof.

As example of C9-hydrocarbon monomers useful to prepare the tackifying resins belonging to class (f) or (g), mention may be made of vinyltoluenes, dicyclopentadiene, indene, methylstyrene, styrene, methylindenes, and any mixture thereof.

According to a particular embodiment of the invention, a mixture of two or more of the above described tackifying resins is used in the hot melt adhesive composition according to the invention.

The tackifying resin(s) (B) used according to the invention are commercially available.

As example of commercially available tackifying resin(s) (B) belonging to class (a), mention may be made of:
  unmodified natural tall oil rosins from KRATON Company sold under the trade names SYLVAROS® (85, 90 and NCY),
  the partially hydrogenated rosin from EASTMAN Company sold under the trade name FORALYN® E and the fully hydrogenated rosin from Eastman sold under the trade name FORAL® AX-E,
  the dimerized rosin from EASTMAN Company sold under the trade name DYMEREX®.

As example of commercially available tackifying resin(s) (B) belonging to class (b), mention may be made of:
  SYLVALITE® RE 100L, a pentaerythritol based tall-oil rosin ester, and
  SYLVALITE® RE 85L, a glycerol ester of tall oil rosin, both available from KRATON Company.

As example of commercially available tackifying resin(s) (B) belonging to class (c), mention may be made of:
  the polyterpene tackifiers from KRATON Company sold under the trade names SYLVAGUM® TR and SYLVARES® TR series (7115, 7125, A25L, B115, M1115).

As example of commercially available tackifying resin(s) (B) belonging to class (d), mention may be made of:
  the terpene phenol resins from KRATON Company sold under the trade names SYLVARES® TP (96, 2040, 300, 7042, 2019).

As example of commercially available tackifying resin(s) (B) belonging to class (e), mention may be made of:
  the aliphatic and cycloaliphatic petroleum hydrocarbon resins based on a C5-petroleum hydrocarbon fraction (such as a mixture of trans-1,3-pentadiene, cis-1,3-pentadiene, 2-methyl-2-butene, dicyclopentadiene, cyclopentadiene, cyclopentene), having a Ring and Ball softening point ranging from 60° C. to 140° C., from EASTMAN Company sold under the trade names WINGTACK® 98, WINGTACK® ET and from EXXONMOBIL sold under the trade name ESCOREZ® 1310LC,
  the partially aliphatic and cycloaliphatic petroleum hydrocarbon resins based on a C5-petroleum hydrocarbon fraction (such as a mixture of trans-1,3-pentadiene, cis-1,3-pentadiene, 2-methyl-2-butene, dicyclopentadiene, cyclopentadiene, cyclopentene), having a Ring and Ball softening point ranging from 80° C. to 140° C., from KOLON Company sold under the trade names SUKOREZ® SU210 and SUKOREZ® 230. The softening point of SUKOREZ® SU210 is 110° C.
  the fully hydrogenated cycloaliphatic petroleum hydrocarbon resins based on a dicyclopentadiene-petroleum hydrocarbon fraction, having a Ring and Ball softening point ranging from 60° C. to 140° C., from EXXONMOBIL sold under the tradename ESCOREZ® 5400 series (5400, 5415, 5490). The softening point of ESCOREZ® 5400 is 100° C.

As example of commercially available tackifying resin(s) (B) belonging to class (f), mention may be made of:
  the aromatic petroleum hydrocarbon resins based on a C9-hydrocarbon petroleum fraction (such as a mixture of vinyltoluenes, dicyclopentadiene, indene, methylstyrene, styrene, methylindenes), having a Ring and Ball softening point of from about 60° C. to 140° C., available from KOLON INDUSTRIES sold under the trade names HIKOTACK® (P-90, P110 S and P120 S).

As example of commercially available tackifying resin(s) (B) belonging to class (g), mention may be made of:
  the partially hydrogenated cycloaliphatic modified aromatic petroleum hydrocarbon resins based on C5/C9-hydrocarbon petroleum fractions, having a Ring and Ball softening point of from about 60° C. to 140° C., from EXXONMOBIL Company sold under the tradename ESCOREZ® 5600 series (5600, 5615, 5690). The softening point of ESCOREZ® 5600 is 100° C.
  the non hydrogenated aliphatic modified aromatic hydrocarbon petroleum resin based on C5/C9-hydrocarbon petroleum fractions sold by ZEON under the trade name QUINTONE® DX390N, with a softening point of 93° C.

According to a preferred embodiment, the Ring and Ball (or softening point) of the tackifying resin(s) (B) preferably lies in the range from 90° C. to 125° C., and even more preferably in the range from 90° C. to 115° C.

The softening temperature (or point) is determined in accordance with the standardized ASTM E 28 test, the principle of which is as follows. A brass ring about 2 cm in diameter is filled with the resin to be tested in the melt state. After cooling to room temperature, the ring and the solid resin are placed horizontally in a thermostatted glycerol bath, the temperature of which may vary by 5° C. per minute. A steel ball about 9.5 mm in diameter is centered on the solid resin disk. The softening temperature is, during the rise in temperature of the bath at a rate of 5° C. per minute, the temperature at which the resin disk flows by an amount of 25.4 mm under the weight of the ball.

The total amount of tackifying resin(s) (B) used according to the invention preferably ranges from 20% to 60% by weight, and more preferably from 45% to 60% by weight, relative to the total weight of the hot melt adhesive composition.

Plasticizer (C):

The hot melt adhesive composition according to the invention comprises from 5% to 30% by weight of at least one plasticizer (C) which is selected from a naphthenic oil, a paraffinic oil, polyisobutylene, a benzoate ester, a wax and an acrylic or carboxylic acid modified wax.

The plasticizer(s) (C) may confer good processability to the hot melt adhesive composition. Moreover, the plasticizer(s) (C) may also provide desired viscosity control without substantially decreasing the adhesive strength or the service temperature (temperature of use) of the hot melt adhesive.

Naphthenic oils and paraffinic oils are petroleum based oils which consists in a mixture of naphthenic hydrocarbons (aliphatic, saturated or unsaturated, $C_4$ to $C_7$-member hydrocarbon rings, and preferably aliphatic, saturated or unsaturated, $C_4$ to $C_6$-member rings. As way of example, mention may be made of cycloalkanes such as cyclopentane, cyclohexane, cycloheptane)), paraffinic hydrocarbons (saturated, linear or branched, alkanes) and aromatic hydrocarbons (aromatic hydrocarbon rings, which may be monocyclic or polycyclic, and preferably aromatic $C_6$-member hydrocarbon rings).

The classification of Naphthenic and Paraffinic oil is made based on the amount of each type of hydrocarbons in the oil. Typically, paraffinic oils have a paraffinic hydrocarbons content of at least 50% by weight; naphthenic oils have a naphthenic hydrocarbons content between 30% and 40% by weight, relative to the total weight of the plasticizer.

Preferably the plasticizer(s) (C) comprised in the composition according to the invention is a naphthenic oil.

Useful plasticizers (C) are commercially available. By way of example, mention may be made of the naphtenic oils from NYNAS sold under the trade names NYFLEX® 223 and NYFLEX® 222B, which are preferably used.

Other plasticizer(s) may be added in the hot melt adhesive composition according to the invention in order to confer comparable or improved advantages to plasticizer (C) as mentioned above. Among these other plasticizers the following products may be cited:
- a polyisobutylene, such as INDOPOL H300, a liquid polybutene available from INEOS oligomers with a molecular weight (Mn) of 1300;
- solid plasticizers such as:
  - a benzoate ester, such as 1,4-cyclohexane dimethanol dibenzoate (Softening point of 118° C.) available from EASTMAN CHEMICAL under the name BENZOFLEX 352;
  - a wax having molecular weight ranging from 1000 to 5000 g/mol such as AC® 617, a polyethylene based wax available from HONEYWELL.
  - an acrylic or carboxylic acid modified wax having molecular weight ranging from 1000 to 5000 g/mol such as AC® 573P, AC® 580 or AC® 596P available from HONEYWELL.

The total amount of plasticizer (C) used according to the invention more preferably ranges from 15% to 25% by weight, relative to the total weight of the hot melt adhesive composition.

Salt of a Hydroxylated Fatty Acid (D):

The hot melt adhesive composition according to the invention comprises from 0.1% to 10% by weight of a salt of a hydroxylated fatty acid (D) comprising from 8 to 24 carbon atoms.

The hydroxylated fatty acid may be saturated, unsaturated or partially unsaturated and may comprise from 1 to 3 hydroxyl functions, preferably 1 or 2 hydroxyl functions.

Mention may be made, as hydroxylated fatty acid which can be used in the invention, of the following hydroxylated fatty carboxylic acids:
saturated linear monohydroxylated monoacids of formulae:

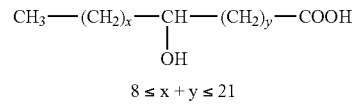

$8 \leq x+y \leq 21$ such as 2-hydroxyoctanoic acid, 3-hydroxyoctanoic acid, 3-hydroxydecanoic acid, 2-hydroxydodecanoic acid, 2-hydroxytetradecanoic acid, 2-hydroxyhexadecanoic acid, α-hydroxystearic acid, β-hydroxylauric acid, β-hydroxymyristic acid, β-hydroxypalmitic12-hydroxyoctadecanoic acid, or HO—$CH_2$—$(CH_2)_z$—COOH

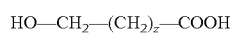

$6 \leq z \leq 20$ such as 10-hydroxydecanoic acid, 11-hydroxyundecanoic, 15-hydroxypentadecanoic acid and 16-hydroxyhexadecanoic acid (or juniperic acid). Such saturated fatty acids are commercially available, for instance from SIGMA-ALDRICH;
saturated branched monohydroxylated fatty acids of formula:

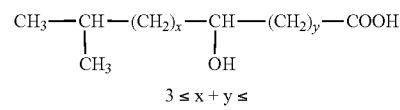

$3 \leq x+y \leq$ 19 such as 2-ethyl-3-hydroxycaprylic acid;
saturated polyhydroxylated fatty acids of formula:

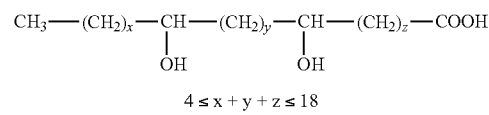

$4 \leq x+y+z \leq 18$ such as 9,10-dihydroxyoctadecanoic acid and 9,12-dihydroxyoctadecanoic acid;
unsaturated monohydroxylated fatty acids of formulae:

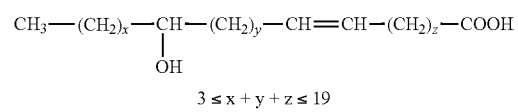

$3 \leq x+y+z \leq 19$ such as 10-hydroxy-2-decenoic, 2-hydroxy-15-tetracosenoic acid (or hydroxynervonic acid) and 12Z-hydroxy-9-octadecanoic acid (or ricinoleic acid), 14Z-hydroxy-11-eicosenoic acid (or lesquerolic acid); or HO—$CH_2$—$(CH_2)_x$—CH=CH—$(CH_2)_y$—COOH

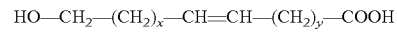

$4 \leq x+y \leq 20$ such as 16-hydroxy-6-hexadecenoic acid whose synthesis has been described in Helvetica Chimica Acta, volume 25, pages 965-77 (1942), or:

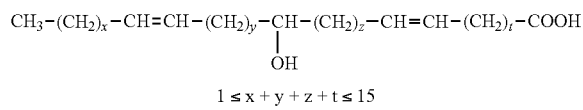

$1 \leq x+y+z+t \leq 15$ such as 12-hydroxy-9Z,15Z-octadecadienoic acid (or Densipolic acid) and 14-hydroxy-11Z,17Z-eicosadienoic acid (or Auricolic acid).

When the hydroxylated fatty acid is saturated, it preferably comprises from 8 to 18 carbon atoms.

Unsaturated monohydroxylated fatty acids such as Densipolic, Auricolic acids and Ricinoleic are preferred, and among them, ricinoleic acid is more particularly preferred, of formula:

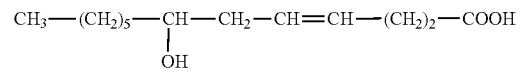

Densipolic and Auricolic acids are respectively monounsaturated and hydroxylated C18 and C20 fatty acids which can be easily obtained from hydrolyzed *Lesquerella densipiia* oil. *Lesquerella densipila* oil is a vegetable oil which is obtained from *Lesquerella densipila* seeds and is composed essentially of triglyceride (triple esters of glycerol) of Densipolic and Auricolic acids.

Ricinoleic acid is a monounsaturated and hydroxylated C18 fatty acid which can be easily obtained from hydrolyzed castor oil. Castor oil is a vegetable oil which is obtained from castor seeds and is composed essentially of triglyceride (triple esters of glycerol) of ricinoleic acid.

When the hydroxylated fatty acid is partially unsaturated, it may be prepared from the unsaturated fatty acids which are available from natural sources such as sunflower, oil seed rape or soybean by an intermediate epoxidation, such as described in the patent FR 2,617,839 of ONIDOL, ITERG and CETIOM.

The salt (D) of the fatty acid which is comprised in the hot-melt adhesive composition according to the invention is preferably a metallic salt, and more preferably a salt (D) with a melting point less than 120° C., advantageously less than 90° C.

A particular preferred embodiment for (D) is the Zinc or Calcium ricinoleate.

The amount of the salt (D) of the fatty acid preferably ranges from 3 to 10%, more preferably from 3 to 8% by weight, relative to the total weight of the hot melt adhesive composition.

Optional Ingredients:
Endblock Reinforcing Resin (E):

When the hot melt adhesive composition according to the invention is intended to be used for highly demanding application which requires a high cohesion of the adhesive joint bonding the 2 assembled substrates, the composition preferably comprises at least one endblock reinforcing resin (E).

The endblock reinforcing resin (E) is primarily aromatic resins based on pure or mixed monomer streams of aromatic monomers. Typical examples of such aromatic monomers include aromatic C9-hydrocarbon monomer, styrene, alpha-methyl styrene, vinyl toluene. Preferred are those based on alpha-methyl styrene.

Useful end block reinforcing resins (E) are commercially available under a variety of trade names including, e.g PLASTOLYN® series from EASTMAN CHEMICAL The endblock reinforcing resin (E) used according to the invention typically has a molecular weight from 5000 to 15000 g/mol.

The Ring and Ball Softening Points of the aromatic endblock resin (E) ranges preferably from 90° C. to 160° C., more preferably, from 100° C. to 140° C., and more preferably from 120° C. to 140° C.

When the endblock reinforcing resin (E) is (are) present in the hot melt adhesive composition according to the invention, its total amount preferably ranges from 3 to 20% by weight, and more preferably from 5 to 15% by weight, relative to the total weight of the hot melt adhesive composition.

Antioxidant (F):

Preferably, the hot melt adhesive composition according to the invention comprises from 0.1% to 2% by weight of at least one antioxidant (F), relative to the total weight of the hot melt adhesive composition.

The antioxidant (F) useful according to the invention is preferably incorporated in the hot melt adhesive composition to help protect the hot melt adhesive composition from chemical degradations. Said degradations generally involve the reactions of free radicals, resulting from chain scission catalyzed either by ultraviolet light or heat, with dioxygen. Such degradation is usually manifested by a deterioration in the appearance (browning of color) or other physical properties of the adhesive, and in the performance characteristics of the adhesive.

In particular, the antioxidant(s) (F) protects the adhesive from the effect of thermal degradations reactions which mainly occur during the manufacturing and application process of the adhesive where the hot melt adhesive composition and its ingredients are heated for a long time at high temperature in presence of dioxygen.

Useful antioxidant(s) (F) include hindered phenols and sulfur and phosphorus containing phenols. Hindered phenols are well known to those skilled in the art and may be characterized as phenolic compounds which also contain sterically bulky groups in close proximity to the phenolic hydroxyl group thereof. In particular, tertiary butyl groups generally are substituted onto the benzene ring in at least one of the ortho positions relative to the phenolic hydroxyl group.

Representative hindered phenols include:
1,3,5-trimethyl-2,4,6-tris(3-5-di-tert-butyl-4-hydroxy-benzyl) benzene; pentaerythritol tetrakis-3(3,5-di-tert-buty 1-4-hydroxyphenyl) propionate; n-octadecyl-3(3, 5-ditert-butyl-4-hydroxyphenyl) propionate;
4,4'-methylenebis(4-methyl-6-tert-butylphenol); 4,4'-thiobis(6-tert-butyl-o-cresol);
2,6-di-tert-butylphenol;
6-(4-hydroxyphenoxy)-2,4-bis(n-octylthio)-1,3,5-triazine; 2,4,6-tris(4-hydroxy-3,5-di-tert-butyl-phenoxy)-1, 3,5-triazine;
di-n-octadecyl-3,5-di-tert-butyl-4-hydroxybenzylphosphonate; 2-(n-octylthio)ethyl-3,5-di-tert-butyl-4-hydroxybenzoate; sorbitol hexa-(3,3,5-di-tert-butyl-4-hydroxy-phenyl) propionate;
2,2'-methylene bis(4-methyl-6-tert-butylphenol)phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP);
tetrakis(methylene(3,5-di-ter-butyl-4-hydroxyhydrocinnamate)) methane; (tris(2,4-ditert-butylphenyl)phosphate), and combinations thereof.

The hindered phenol antioxidants may be used by themselves or in combination with other antioxidants, such as phosphites antioxidants like IRGAFOS® series, or aromatic amine antioxidants like NAUGARD® series from ADDIVANT.

Useful antioxidants E are commercially available under a variety of trade designations including, e.g., the hindered phenolic antioxidants of IRGANOX® series from BASF including, e.g., IRGANOX® 1010 (tetrakis(methylene(3,5-di-ter-butyl-4-hydroxyhydrocinnamate)) methane), and IRGAFOS® 168 antioxidant (tris(2,4-ditert-butylphenyl) phosphate).

The total amount of antioxidant(s) (F) is preferably ranging from 0.1 to 3% by weight, and more preferably from 0.5% to 1% by weight, relative to the total weight of the hot melt adhesive composition.

The performance of the antioxidants useful according to the invention may be further enhanced by utilizing, in conjunction therewith: (1) synergists such as, for example, thiodipropionate esters and phosphites; and/or (2) chelating agents and metal deactivators as, for example, ethylenediamine tetraacetic acid, salts thereof, and disalicylalpropylenediimine.

Other optional ingredient(s) may be incorporated into the hot melt adhesive composition according to the invention in order to modify some of its physical properties.

Among the optional ingredients, mention may be made of fillers, surfactants, colorants, ultraviolet light stabilizers, fluorescent agents, rheology modifiers, and the like.

The total amount of these optional ingredient(s) may range from 0% to 10% by weight, preferably from 0.1% to 5% by weight, and more preferably from 0.1% to 2% by weight, relative to the total weight of the hot melt adhesive composition.

According to a preferred embodiment, the hot melt adhesive composition according to the invention comprises, and preferably consists essentially of:
  a) from 15% to 45% by weight of the thermoplastic polymer (A);
  b) from 20% to 60% by weight of the tackifying resin (B);
  c) from 15% to 25% by weight of the plasticizer (C); and
  d) from 3% to 10% by weight of the salt (D) of hydroxylated fatty acid.

According to an even more preferred embodiment, the hot melt adhesive composition according to the invention comprises, and preferably consists essentially of:
  a) from 15% to 25% by weight of the thermoplastic polymer (A);
  b) from 45% to 60% by weight of the tackifying resin (B);
  c) from 15% to 25% by weight of the plasticizer (C); and
  d) from 3% to 8% by weight of the salt (D) of hydroxylated fatty acid.

According to a second object of the invention, the present application relates to a process of manufacture of the hot melt adhesive composition according to the invention comprising at least a step of mixing and heating at a temperature ranging from 140° C. to 170° C. the ingredients of the hot melt adhesive composition according to the invention, at least for a period of time long enough to melt the tackifying resin(s) (B) and the thermoplastic polymer(s) (A).

The hot melt adhesive composition of the present invention may be produced using any of the techniques known in the art. The ingredients used are preferably mixed and heated at high temperature for at least several hours, typically at least 4 hours, and preferably from 4 to 6 hours, at a temperature ranging from 140 to 170° C.

The hot melt adhesive composition according to the invention can be prepared in presence of dioxygen (such as under air atmosphere), or preferably under inert atmosphere e.g. under carbon dioxide or nitrogen to limit potential degradation by oxidative reactions.

According to a preferred embodiment, the process to manufacture the hot melt adhesive composition according to the invention comprises:
  a first step of mixing and heating the tackifying resin(s) (B), and the plasticizer(s) (C), preferably with the antioxidant(s) (F) when present, at a temperature ranging from 120° C. to 140° C., at least for a period of time long enough to melt all the tackifying resin(s) (B),
  a second step of adding the thermoplastic polymer (s) (A) into the mixture obtained in the previous step under stirring and heating at a temperature ranging from 150° C. to 170° C., at least for a period of time long enough to melt all the thermoplastic polymer(s) A,
  the salt (D) of the hydroxylated fatty acid being possibly added either during the first step or during the second step in mixture with the other ingredients, or subsequently during a subsequent third step in the hot melt adhesive composition resulting from the second step at a temperature ranging from 130° C. to 150° C. under stirring.

Preferably, the salt (s) (D) are added in the third step, at it has low melting temperature.

Additionally, the process of the invention may comprise a step of applying vacuum to remove any entrapped air in the mixture, before or after any of the step of process described previously.

Other useful optional ingredient(s) which may be present in the hot melt adhesive composition according to the invention may be added at any step of the process according to the invention.

The hot melt adhesive composition according to the invention, prepared by the above-described process may further be kept, for example in a melting kettle, under melted state for up to an additional 15 hours before being cooled down and packaged in form of a ready-to-use solid composition.

According to a third object of the invention, the present application relates to a process of manufacturing an assembly product (or laminate) comprising:
  a step (i) of heating at a temperature ranging from 130° C. to 180° C. the hot melt adhesive composition according to the invention, for at least a period of time long enough to render the hot melt adhesive composition liquid enough to be applied on a substrate (for example at least two hours at industrial scale), then
  a step (ii) of coating said composition on a first substrate, then
  a step (iii) of putting into contact the coated surface of the first substrate with the surface of a second substrate, so as to form an adhesive joint bonding the two substrates.

The substrates may be different or of same nature, with various forms (layer or film, strands, fluff)

Preferably each substrate may be chosen independently from one another among nonwoven fabric, tissue, absorbent fluff, super absorbent polymer (SAP), composite material, plastics which may be elastomeric or non elastomeric, and which may be chosen for example from Styrene Block Copolymers (SBC), Polyurethane, and Polyolefin, and any mixture thereof. The composite material may be made of at least one of the above-mentioned materials.

The hot melt adhesive composition according to the invention can be coated or applied with a variety of application techniques known in the art, which include contact type application (such as slot die coating) and non-contact type application (such as spraying or fiberization).

In particular, as mentioned above, the hot melt adhesive composition according to the invention can be applied easily through conventional coating nozzles, such as those having a diameter from 0,305 to 0,762 mm or a slot die length adjustable by a shim and ranging from 20 μm to 300 μm.

The amount of coated adhesive by surface unit can vary in a very large range from 0.1 to 50 gsm (Gram by Square Meter), depending on the substrates intended to be bonded. For example one may cite a range from 0.2 to 1 gsm in case of nonwoven substrates bonded with the polyethylene film to produce the cloth-like backsheet assembly, while a range from 3 to 7 gsm can be used in case of the assemblies of the disposable multilayers. A much higher range, from 20 to 40 gsm, can also be used when high shear performance is requested, like for instance for bonding ears to the diaper chassis.

Before being applied on the surface of the first substrate, the hot melt adhesive composition according to the invention may further be kept in a melting kettle for up to 4 days. The hot melt adhesive composition according to the invention can be applied on a substrate or stored in presence of dioxygen (under air atmosphere), or preferably under inert atmosphere to limit degradations due to oxidative reactions.

According to a fourth object of the invention, the present application relates to an assembly product comprising at least two substrates bonded by at least one hot melt adhesive composition according to the invention.

The substrates bonded may be chosen among the substrates listed above for the process of applying the hot melt adhesive composition, according to the invention.

The hot melt adhesive composition according to the invention may be used as the laminating adhesive to bind a plurality of substrate layers for example to manufacture toilet tissues, paper towels, wipes and other consumer products, particularly absorbent articles such as disposable hygiene products, and more particularly disposable diapers.

In a particular embodiment of the invention, the assembly product according to the invention may be a multilayer product comprising at least two layers of substrate(s) bonded by at least one hot melt adhesive composition according to the invention.

In the assembly product according to the invention, the at least two layers of substrate(s) may be joined adhesively by a layer of hot melt adhesive composition according to the invention, in sandwich between the two layers of substrate(s).

Alternatively or cumulatively, the at least two layers of substrate(s) may be joined adhesively by spots of hot melt adhesive composition according to the invention.

Preferably, the assembly product is a disposable nonwoven absorbent article.

According to a fifth object of the invention, the present application relates to a process for cleaning the metallic parts of a laminating device fouled by solid deposits of the hot melt adhesive composition according to the invention, said process comprising the manual removal of said deposits by the operators at room temperature.

For instance use can be made of a cloth optionally soaked with a solvent or of a metallic brush to wipe out the solid deposits.

The following examples are given purely by way of illustration of the invention and should not, under any circumstances, be interpreted as limiting the scope thereof.

EXAMPLE 1 (REFERENCE)

The composition in Table 1 is prepared by simple mixing of its ingredients as pointed out above in the detailed description of the invention.

This adhesive composition is submitted to the following tests and measurements.

A. Loop Tack Test on Stainless Steel:

The loop tack of the adhesive composition is determined by the loop tack test on stainless steel described in FINAT Test Method No. 9.

A.1. Preliminary Preparation of a Support Coated by the Adhesive Composition of Example 1:

Use is made as a laminating device of a machine operating continuously at a line speed of approximately 20 m/minute, which machine is sold by ACUMETER Laboratory Inc. In this machine the coating nozzle is a slot nozzle.

The support employed is a 50 µm thick PET film (Mylar®) with a width of 15 cm.

The adhesive composition is heated in the melting pot at a temperature of 149° C., then is coated on the PET film as a 5 cm wide adhesive layer with a coating weight of 20 g/m², which is centered on said PET film. A 15 cm wide release liner is then put into contact with the coated surface of the PET film by means of a nip roll applying a pressure of 1 bar.

A rectangular strip measuring 2.5 cm by 17.5 cm is cut out in the coated central area of the laminate, then is conditioned overnight at 23° C. and 50% relative humidity.

A2. Implementation of the FINAT Test Method No. 9:

The release liner is then removed from this strip and its two ends are joined together to form a loop, the adhesive layer of which is facing outward.

The two joined ends are placed in the movable jaw of a tensile testing machine capable of imposing a rate of displacement of 300 mm/minute along a vertical axis, with the possibility of forming a forward-and-backward movement. The lower part of the loop placed in the vertical position is firstly put into contact with a horizontal stainless steel plate measuring 2.5 cm by 3 cm over a square area measuring about 2.5 cm per side.

Once this contact has occurred, the displacement direction of the jaw is reversed.

The loop tack is the maximum value of the force needed for the loop to be completely debonded from the plate, and is measured in Newton (N).

It is reported in Table 2 below.

B. Peel Test on a Laminate Comprising a PE and a Non Woven PP:

B.1. Preliminary Preparation of a Laminate Bonded by the Adhesive Composition of Example 1:

Use is made, as a laminating device, of a machine operating continuously at a line speed of approximately 200 m/minute, which machine is sold by NORDSON under the name of Coater CTL 4400.

In this machine, the coating nozzle is a spray nozzle (NORDSON Signature™).

The two substrates employed are:
- a 20 µm thick PE film which has been previously laminated on a non woven sheet to give a cloth like back-sheet and which has a width of 20 cm, and
- a 14 g/m² spunmelt nonwoven sheet of the same width, which is composed of fibers of polypropylene (PP).

These two substrates are packaged as a reel with a width of 20 cm.

The adhesive composition is heated in the melting pot at a temperature of 149° C.

It is then coated at 2 different coating weights of approximately 3 g/m² and 5 g/m² on the PE side of the cloth like back-sheet film. The coating pattern is a 2.54 cm wide non continuous layer made of adhesive fibers, which is centered on said PE film and along an axis which is perpendicular to the axis of the reel.

The nonwoven (PP) sheet is then put into contact with the coated surface of the PE film by means of a nip roll applying a pressure of 1 bar.

B.2. Peel:

The assembly obtained is then packaged as a reel and left for 24 hours at ambient temperature and at 50% relative humidity.

A rectangular strip measuring 2.54 cm by approximately 10 cm is then cut out in the coated central area of the laminate.

The two individual substrates are separated, starting from one end of the above rectangular strip (as a test specimen) and over approximately 2 cm.

The two free ends thus obtained are fixed to two clamping devices respectively connected to a stationary part and a movable part of a tensile testing device which are located on a vertical axis.

While a drive mechanism communicates, to the movable part, a uniform speed of 300 mm/minute, resulting in the separation of the two substrates, the separated ends of which are gradually displaced along a vertical axis while forming an angle of 180°, the stationary part, connected to a dynamometer, measures the force withstood by the test specimen thus held.

The result for each coating weight, corresponding to the peel after 24 hours at ambient temperature, is expressed in N.

The peel after, respectively, 1 month at ambient temperature and 1 month at a temperature of 55° C., is measured by repeating the above protocol except that the assembly obtained after lamination is left during the respective time at the corresponding temperature.

The results are reported in Table 2 below.

C. Shear Test on a Laminate Comprising 2 Non Woven PP:

The level of cohesion of the laminated assembly is also evaluated by the shear test, the principle of which consists of the determination of the force necessary for the separation by shear of two substrates bonded by the adhesive composition.

C.1. Preliminary Preparation of a Laminate Bonded by the Adhesive Composition of Example 1:

Use is made, as a laminating device, of a machine operating continuously at a line speed of approximately 200 m/minute, which machine is sold by NORDSON under the name of Coater CTL 4400.

In this machine, the coating nozzle is a slot nozzle, NORDSON Slot™.

The two substrates employed are identical and consist of a 40 g/m² melt blown nonwoven sheet with a width of 20 cm composed of fibers of polypropylene (PP).

These two identical substrates are packaged as a reel with a width of 20 cm.

The adhesive composition is heated in the melting pot at a temperature of 149° C., then is coated on 2 cm from the right edge of the first substrate, resulting in the deposition over said edge of a continuous layer with a width of 1.5 cm corresponding to an amount of approximately 15 g/m², which layer is positioned perpendicular to the axis of the reel.

The second substrate is then laminated over the first substrate by means of a nip roll applying a pressure of 1 bar, in such a way that the adhesive layer is 2 cm from its left edge.

C2. Shear:

The assembly obtained is then packaged as a reel and left for 24 hours at ambient temperature and at 50% relative humidity.

The laminated substrates with a total width of about 35 cm and assembled by the 1.5 cm wide coated region are then cut out in the cross direction, so as to obtain a test specimen of rectangular shape with a length of approximately 35 cm and a width of 2.54 cm The first substrate of the specimen is then hung secure in an oven at 37.8° C., while a 500 g weight is attached to the secondary substrate.

The time after which the assembly fails, corresponding to the shear after 24 hours at ambient temperature, is recorded in minutes.

The shear after 1 month at ambient temperature is measured by repeating the above protocol except that the assembly obtained after lamination is left during the corresponding time and temperature.

The results are reported in Table 2 below.

D. Viscosity Change Test:

Initial viscosity of the adhesive composition is measured at a temperature of 149° C. in accordance with ASTM D-3236 using a Brookfield Thermosel viscometer and a number 27 spindle. The spindle speed was adjusted so that the percent torque was between 45% and 90%. The results are reported in centipoise (cP).

Then, 200 grams of the adhesive composition is placed in a 400-ml glass jar and covered by an aluminum foil.

The jar is aged at 149° C. for 72 hours, in order to simulate adhesive aging in the melting tank.

A 10 g sample of the adhesive composition is removed at various times (24 h, 48 h, 72 h) during aging and the viscosity is measured at a temperature of 149° C. using the same method as for the initial viscosity.

The viscosity change at the aged time (or Final viscosity) is calculated according to the following equation and is expressed in percent:

$$\text{Viscosity change} = ((\text{Final viscosity} - \text{Initial viscosity}) * 100 / (\text{Initial viscosity}))$$

The result is reported in Table 2 below.

EXAMPLE 2 (ACCORDING TO THE INVENTION)

Example 1 is repeated with the composition of example 2 shown in Table 1.

The results for the loop tack test, the peel test, the shear test and viscosity change are reported in Table 2 below.

One can observe a very significant drop (by a factor 4) of the room temperature tack on stainless steel, by reference with Example 1, which shows that the hot melt adhesive composition has a strongly reduced adhesion on metallic substrates.

The results of peel and shear are comparable to those obtained for the reference example 1, showing in particular a strong adhesion on polymeric substrates.

With respect to the viscosity change, it appears that the composition of example 2 is just as stable as the composition of reference example 1, making it just as suited for remaining in a coater melting tank during up to three days.

EXAMPLE 3 (REFERENCE)

The composition in Table 1 is prepared by simple mixing of its ingredients as pointed out above in the detailed description of the invention.

This adhesive composition is submitted to the loop tack test on stainless steel, the peel test, the viscosity change test such as previously described.

The results are reported in Table 2 below.

This adhesive composition is also submitted to the following test.

E. Test of Delamination from an Aluminium Foil:

E.1. Preliminary Preparation of a Laminate Bonded by the Adhesive Composition of Example 3:

The protocol of A.1. above is repeated by simply replacing the release liner by an aluminium foil with a thickness of 20 μm.

E.2. Peel:

The peel measurement is then implemented as described above in B.2.

The result, corresponding to the delamination from aluminium foil, is expressed in N.

It is reported in Table 2 below.

EXAMPLE 4 (ACCORDING TO THE INVENTION 1)

Example 3 is repeated with the composition of example 4 shown in Table 1.

The results of the loop tack test, the delamination from aluminium foil test, the peel test and the viscosity change test are reported in Table 2 below.

One can observe for the loop tack on stainless steel a significant drop (by a factor 3), with respect to reference example 3. One can also observe a significant drop (by a factor of 2) of the force necessary to delaminate from the aluminium foil, by reference with Example 3. These two results show that the hot melt adhesive composition has a strongly reduced adhesion on metallic substrates.

The results of peel for each of the 2 coating weights are comparable to those obtained for the reference example 3, showing in particular a strong adhesion on polymeric substrates.

With respect to the viscosity change, it appears that the composition of example 4 is just as stable as the composition of reference example 3, making it just as suited for remaining in a coater melting tank during up to three days.

TABLE 1

| Ingredients | Example 1 (ref.) | Example 2 | Example 3 (ref.) | Example 4 |
|---|---|---|---|---|
| (A) KRATON ® D1152 ES | — | — | 18.7 | 17.8 |
| (A) INFUSE ® 9807 | 11.7 | 11.1 | — | — |
| (A) AFFINITY ® GA 1900 | 11 | 10.5 | — | — |
| (B) QUINTONE ® DX390N | — | — | 30 | 28.6 |
| (B) ESCOREZ ® 5600 | — | — | 14.2 | 13.5 |
| (B) ESCOREZ ® 5400 | — | — | 14.1 | 13.4 |
| (B) SUKOREZ ® SU210 | 55.1 | 52.5 | — | — |
| (C) NYFLEX ® 223 | 21.3 | 20.3 | 22.5 | 21.4 |
| (D) Zinc ricinoleate | — | 4.8 | — | 4.8 |
| (F) IRGANOX ® 1010 | 0.9 | 0.8 | 0.5 | 0.5 |

TABLE 2

| | | Example 1 (ref.) | | Example 2 | | Example 3 (ref.) | | Example 4 | |
|---|---|---|---|---|---|---|---|---|---|
| Loop tack on stainless steel (N) | | 8.3 | | 2.0 | | 22.5 | | 6.6 | |
| Delamination from aluminium foil | | NT* | | NT* | | 11.2 | | 5.6 | |
| Peel (N) | Coating weight (g/m²) | 3 | 5 | 3 | 5 | 3 | 5 | 3 | 5 |
| | after 24 hours at ambient temperature | 1.42 | 1.7 | 1.48 | 2.14 | 1.1 | 2.48 | 1.13 | 2.39 |
| | after 1 month at ambient temperature | 1.16 | 2.18 | 1.30 | 2.46 | NT* | 2.2 | NT* | 2.02 |
| | after 1 month at 55° C. | 0.88 | 1.55 | 0.85 | 1.57 | NT* | NT* | NT* | NT* |
| Shear (minutes) | after 24 hours at ambient temperature | 6.5 | | 7.5 | | NT* | | NT* | |
| | after 1 month at ambient temperature | 9.3 | | 16.5 | | NT* | | NT* | |
| Viscosity change (%) | at 24 hours | −0.9 | | +2 | | −5.5 | | −5.7 | |
| | at 48 hours | +1.8 | | +1.4 | | −13 | | −10.7 | |
| | at 72 hours | +0.9 | | +0.85 | | −18 | | −19.2 | |

*NT means Not Tested

The invention claimed is:

1. A hot melt adhesive composition comprising:
   a) 5% to 50% by weight of at least one thermoplastic polymer (A) selected from styrene block copolymers (SBC) and polyolefins;
   b) 15% to 60% by weight of at least one tackifying resin (B);
   c) 5% to 30% by weight of at least one plasticizer (C) selected from a naphthenic oil, a paraffinic oil, polyisobutylene, a benzoate ester, a wax and an acrylic or carboxylic acid modified wax; and
   d) 3% to 10% by weight of a salt (D) of a hydroxylated fatty acid comprising 8 to 24 carbon atoms.

2. The hot melt adhesive composition according to claim 1, wherein the thermoplastic polymer (A) is a linear triblock styrene-butadiene-styrene copolymer (SBS).

3. The hot melt adhesive composition according to claim 1, wherein the thermoplastic polymer (A) is a copolymer of ethylene and α-olefin monomers.

4. The hot melt adhesive composition according to claim 1, wherein the tackifying resin (B) is selected from:
   (a) natural and modified rosins;
   (b) glycerol and pentaerythritol esters of natural and modified rosins;
   (c) polyterpene resins;
   (d) phenolic-modified terpene resins;
   (e) aliphatic petroleum hydrocarbon resins (C5) having a Ring and Ball softening point of about 60° C. to 140° C., and corresponding hydrogenated derivatives;
   (f) aromatic petroleum hydrocarbons resins (C9) having Ring and Ball softening point of about 60° C. to 140° C., and corresponding hydrogenated derivatives; and
   (g) aliphatic and/or aromatic petroleum resins (C5/C9) having a Ring and Ball softening point of about 60° C. to 140° C., and corresponding hydrogenated derivatives.

5. The hot melt adhesive composition according to claim 1, wherein the softening point of the tackifying resin (B) is 90° C. to 125° C.

6. The hot melt adhesive composition according to claim 1, wherein the hydroxylated fatty acid is ricinoleic acid.

7. The hot melt adhesive composition according to claim 1, wherein the salt (D) of hydroxylated fatty acid is a metallic salt with a melting point less than 120° C.

8. The hot melt adhesive composition according to claim 1, wherein the salt (D) of hydroxylated fatty acid is Zinc or Calcium ricinoleate.

9. The hot melt adhesive composition according to claim 1, comprising:
   a) 15% to 45% by weight of the thermoplastic polymer (A);
   b) 20% to 60% by weight of the tackifying resin (B);
   c) 15% to 25% by weight of the plasticizer (C); and
   d) 3% to 10% by weight of the salt (D) of hydroxylated fatty acid.

10. A process for preparing the hot melt adhesive composition according to claim 1, comprising at least a step of mixing and heating at a temperature of 140° C. to 170° C. the thermoplastic polymer (A), the tackifying resin (B), the plasticizer (C) and the thermoplastic polymer (A), for at least a period of time long enough to melt the tackifying resin (B) and the thermoplastic polymer (A).

11. The process of preparing an assembly product comprising:
   a step (i) of heating at a temperature of 130° C. to 180° C. the hot melt adhesive composition according to claim 1, for at least a period of time long enough to render said hot melt adhesive composition liquid enough to be applied on a substrate, then
   a step (ii) of coating said composition on a first substrate, and
   a step (iii) of putting into contact the coated surface of the first substrate with the surface of a second substrate, so as to form an adhesive joint bonding the two substrates.

12. The process of preparing according to claim 11, wherein each substrate is chosen independently from one another from nonwoven fabric, tissue, absorbent fluff, super absorbent polymer (SAP), composite material, elastomeric and non elastomeric plastics.

13. An assembly product comprising at least two substrates bonded by at least one hotmelt adhesive composition according to claim 1.

14. The assembly product according to claim 13, which is a disposable nonwoven absorbent article.

15. A process for cleaning metallic parts of a laminating device fouled by solid deposits of the hot melt adhesive composition according to claim 1, said process comprising the manual removal of said deposits by an operator at room temperature.

16. The hot melt adhesive composition according to claim 1, comprising 3% to 8% by weight of the salt (D) of hydroxylated fatty acid.

17. The hot melt adhesive composition according to claim 1, comprising 8% to 10% by weight of the salt (D) of hydroxylated fatty acid.

18. The hot melt adhesive composition according to claim 1, comprising 4.8% to 8% by weight of the salt (D) of hydroxylated fatty acid.

19. The hot melt adhesive composition according to claim 1, comprising 3% to 4.8% by weight of the salt (D) of hydroxylated fatty acid.

20. The hot melt adhesive composition according to claim 1, comprising, as the hydroxylated fatty acid, 4.8% ricinoleic acid by weight.

* * * * *